United States Patent [19]
Coy et al.

[11] Patent Number: 6,001,801
[45] Date of Patent: Dec. 14, 1999

[54] CYCLIC PEPTIDE ANALOGS OF SOMATOSTATIN

[75] Inventors: David H. Coy, New Orleans, La.; John E. Taylor, Upton, Mass.

[73] Assignees: Biomeasure, Inc., Milford, Mass.; Tulane Univ. Medical Ctr., New Orleans, La.

[21] Appl. No.: 09/006,348

[22] Filed: Jan. 13, 1998

Related U.S. Application Data

[63] Continuation of application No. 08/578,037, Dec. 26, 1995, Pat. No. 5,708,135
[60] Provisional application No. 60/004,633, Sep. 29, 1995.
[51] Int. Cl.[6] .......................... A61K 38/31; A61K 38/12; C07K 7/00
[52] U.S. Cl. ............................... 514/9; 514/11; 530/311; 530/317
[58] Field of Search .................... 530/317, 311; 514/9, 11

[56] References Cited

U.S. PATENT DOCUMENTS

| | | | |
|---|---|---|---|
| 4,133,782 | 1/1979 | Vale, Jr. et al. | 260/8 |
| 4,211,693 | 7/1980 | Rivier et al. | 260/112.5 |
| 4,428,942 | 1/1984 | Rivier et al. | 424/177 |
| 4,798,821 | 1/1989 | Hartmann | 514/9 |
| 4,853,371 | 8/1989 | Coy et al. | 514/12 |
| 5,358,934 | 10/1994 | Borovsky et al. | 514/17 |
| 5,506,339 | 4/1996 | Coy et al. | 530/311 |
| 5,708,135 | 1/1998 | Coy et al. | 530/311 |

FOREIGN PATENT DOCUMENTS

| | | |
|---|---|---|
| 84721/91 | 11/1991 | Australia . |
| 9184721 | 11/1991 | Australia . |
| 900089 | 1/1985 | Belgium . |
| 0021585 | 1/1981 | European Pat. Off. . |
| 0 646 873 A2 | 4/1995 | European Pat. Off. . |
| 2523125 | 9/1983 | France . |
| 24 16 048 | 10/1975 | Germany . |
| 3-252783 | 11/1991 | Japan . |
| 4-227540 | 8/1992 | Japan . |
| 7-134701 | 5/1995 | Japan . |
| WO98/10354 | 3/1998 | WIPO . |

OTHER PUBLICATIONS

Fisher et al., "Somatostatin Analog: Plasma Catecholamine Suppression Mediated by the Central Nervous System" Endocrinology 107:714–718, 1980.

Vale et al., "Biologic and Immunologic Activities and Applications of Somatostatin Analogs", Metabolism 27, No. 9, Suppl. 1, pp. 1391–1401, 1978.

Veber et al., "Highly Active Cyclic and Bicyclic Somatostatin Analogues of Reduced Ring Size", Reprint from Nature 280:512–514, 1979.

*Primary Examiner*—Cecilia J. Tsang
*Attorney, Agent, or Firm*—John D. Conway; Fish & Richardson

[57] ABSTRACT

A cyclic peptide analog of somatostatin wherein a disulfide bond links the N-terminus residue and the C-terminus residue.

16 Claims, No Drawings

CYCLIC PEPTIDE ANALOGS OF SOMATOSTATIN

CROSS REFERENCE TO RELATED APPLICATIONS

This is a continuation of U.S. application Ser. No. 08/578,037, filed Dec. 26, 1995, now U.S. Pat. No. 5,708,135 which claims the benefit of prior U.S. provisional application Ser. No. 60/004,633, filed Sep. 29, 1995.

BACKGROUND OF THE INVENTION

Native somatostatin is comprised of both a 14-amino acid isoform (somatostatin-14) and a 18-amino acid isoform (somatostatin-28). Heiman, et al., Neuroendocrinology, 45:429–436 (1987). Because of the short half-life of the native somatostatin, various somatostatin analogs have been developed, e.g., for the treatment of acromegaly. Raynor, et al., Molecular Pharmacol. 43:838 (1993). Five distinct somatostatin receptors have been identified and characterized. Hoyer, et al., Naunyn-Schmiedeberg's Arch. Pharmacol., 350:441 (1994). Somatostatin produces a variety of effects, including modulation of hormone release, e.g., growth hormone, glucagon, insulin, amylin, and neurotransmitter release. Some of these effects have been associated with its binding to a specific somatostatin receptor. For example, the inhibition of growth hormone has been attributed to the somatostatin type-2 receptor ("SSTR-2") (Raynor, et al., Molecular Pharmacol. 43:838 (1993); Lloyd, et al., Am. J. Physiol. 268:G102 (1995)) while the inhibition of insulin has been attributed to the somatostatin type-5 receptor ("SSTR-5") (Coy, et al. 197:366–371 (1993)). It is preferred to have an analog which is selective for the specific somatostatin receptor subtype responsible for the desired biological response, thus, reducing interaction with other receptor subtypes which could lead to undesirable side effects.

SUMMARY OF THE INVENTION

The invention relates to a peptide covered by the following generic formula:

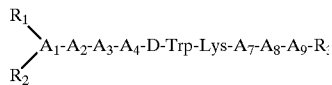

in which
$A_1$ is the D- or L-isomer of Cys;
$A_2$ is Asn, Gln, an aliphatic amino acid, or an aromatic amino acid;
$A_3$ is an aromatic amino acid;
$A_4$ is His or an aromatic amino acid;
$A_7$ is Thr, Ser, or an aliphatic amino acid;
$A_8$ is an aromatic amino acid;
$A_9$ is the D- or L-isomer of Cys;
each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and
$R_3$ is OH, $NH_2$, $C_{1-12}$ alkoxy, or $NH.Y.CH_2.Z$ where Y is a $C_{1-12}$ hydrocarbon moiety (divalent, e.g., straight or branched alkyl group) and Z is H, OH, $CO_2H$, or $CONH_2$; and
a disulfide bond links the side chains of residues $A_1$ and $A_9$; or a pharmaceutically acceptable salt thereof.

In one embodiment, each of $A_3$ and $A_8$, independently, is Phe, p-X-Phe (where X is a halogen, OH, $OCH_3$, $CH_3$, or $NO_2$), o-X-Phe (where X is a halogen, OH, $OCH_3$, $CH_3$, or $NO_2$), pyridyl-Ala, Trp, β-Nal, 2,4-dichoro-Phe, Tyr(I), or $F_5$-Phe, $A_4$ is His, Phe, p-X-Phe (where X is a halogen, OH, $OCH_3$, $CH_3$, or $NO_2$), o-X-Phe (where X is a halogen, OH, $OCH_3$, $CH_3$, or $NO_2$), pyridyl-Ala, Trp, β-Nal, 2,4-dichloro-Phe, Tyr(I), or $F_5$-Phe, $A_2$ is Asn, Gln, Ala, Aib, Val, Leu, Ile, Nle, Nva, Abu, Phe, p-X-Phe (where X is a halogen, OH, $OCH_3$, $CH_3$, or $NO_2$), o-X-Phe (where X is a halogen, OH, $OCH_3$, $CH_3$, or $NO_2$), pyridyl-Ala, Trp, β-Nal, 2,4-dichloro-Phe, Tyr(I), $F_5$-Phe, or is deleted, and $A_7$ is Thr, Ser, Ala, Aib, Val, Leu, Ile, Nle, Nva, or Abu.

In a further embodiment, $A_9$ is Cys, each of $A_3$ and $A_8$, independently, is Phe, p-X-Phe (where X is a halogen, OH, or $CH_3$), Tyr(I), or Trp, $A_4$ is His, Phe, p-X-Phe (where X is a halogen, OH, or $CH_3$), Tyr(I), or Trp, $A_2$ is Asn, Gln, or is deleted, and $A_7$ is Thr or Ser.

In a still further embodiment, $A_2$ is Asn or is deleted, $A_3$ is Phe, $A_4$ is Phe, His, Tyr(I), or Trp, $A_8$ is Phe, and each of $R_1$ and $R_2$, independently, is H, and $R_3$ is $NH_2$.

Below are examples of the peptides of this invention as covered by the above formula:

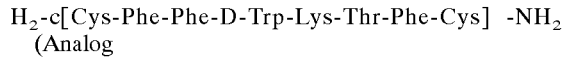
(Analog I),
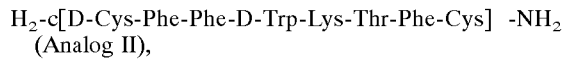
(Analog II),
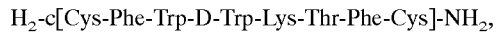
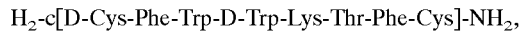
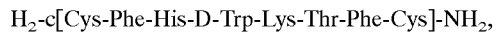
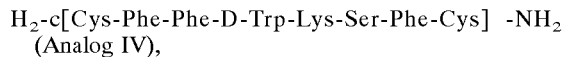
(Analog IV),
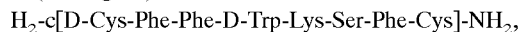
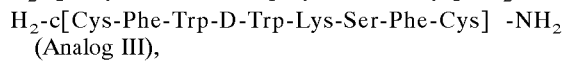
(Analog III),
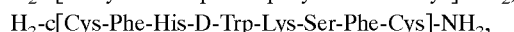
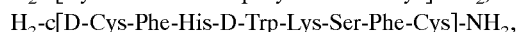
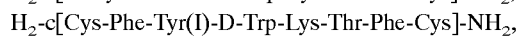
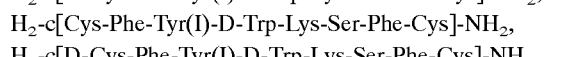
(Analog V),
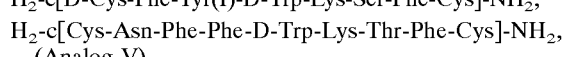
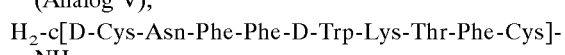
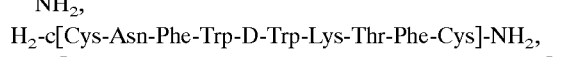
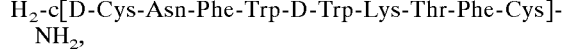
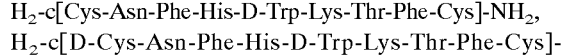
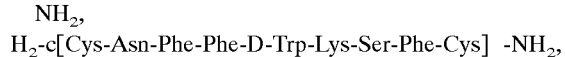
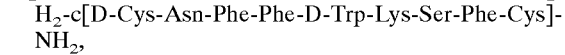
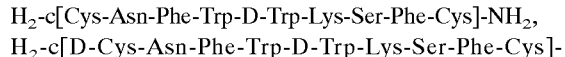
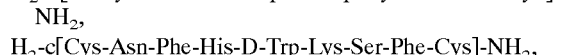
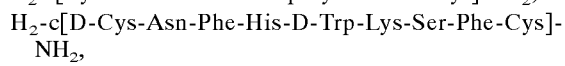

H$_2$-c[Cys-Asn-Phe-Tyr(i)-D-Trp-Lys-Thr-Phe-Cys]-NH$_2$,

H$_2$-c[D-Cys-Asn-Phe-Tyr(I)-D-Trp-Lys-Thr-Phe-Cys]-NH$_2$,

H$_2$-c[Cys-Asn-Phe-Tyr(I)-D-Trp-Lys-Ser-Phe-Cys]-NH$_2$, and

H$_2$-c[D-Cys-Asn-Phe-Tyr(I)-D-Trp-Lys-Ser-Phe-Cys]-NH$_2$.

With the exception of the N-terminal amino acid, all abbreviations (e.g., Ala or A$_2$) of amino acids in this disclosure stand for the structure of —NH—CH(R)—CO—, wherein R is a side chain of an amino acid (e.g., CH$_3$ for Ala). For the N-terminal amino acid, the abbreviation stands for the structure of =N—CH(R)—CO—, wherein R is a side chain of an amino acid. Nle, Nva, pyridyl-Ala, F$_5$-Phe, 2,4-dichloro-Phe, β-Nal, Abu, and Aib are respective abbreviations of the following α-amino acids: norleucine, norvaline, β-pyridyl-alanine, pentafluorophenylalanine, 2,4-dichlorophenylalanine, β-napthylalanine, α-aminobutyric acid, and α-aminoisobutyric acid. Tyr(I) refers to an iodinated tyrosine residue (e.g., 3-I-Tyr, 5-I-Tyr, 3,5-I-Tyr) wherein the iodine may be a radioactive isotope, e.g., I$^{125}$, I$^{127}$, or I$^{131}$. An aliphatic amino acid is an α-amino acid having one or two side chains which, independently, are hydrocarbons, e.g., a straight or branched chain of 1–6 carbons. Examples of aliphatic amino acids include Ala, Aib, Val, Leu, Ile, Nle, Nva, or Abu. An aromatic amino acid is an α-amino acid the side chain of which has a neutral (e.g., not acidic or basic) aromatic substituent, e.g., a substituted or unsubstituted phenyl, naphthyl, or aromatic heterocycle group (e.g., pyridyl or indolyl). Examples of aromatic amino acids include Phe, p-X-Phe (where X is a halogen (e.g., F, Cl, or I), OH, OCH$_3$, CH$_3$, or NO$_2$), o-X-Phe (where X is a halogen, OH, OCH$_3$, CH$_3$, or NO$_2$), pyridyl-Ala, Trp, β-Nal, 2,4-dichloro-Phe, Tyr(I), F$_5$-Phe. Where the amino acid residue is optically active, it is the L-isomer that is intended unless otherwise specified. Also, in the above generic formula, hydroxyalkyl, hydroxyphenylalkyl, and hydroxynaphthylalkyl may contain 1–4 hydroxy substituents, and COE$_1$ stands for —C=O.E$_1$. Examples of —C=O.E$_1$ include, but are not limited to, p-hydroxyphenylpropionyl (i.e., —C=O.CH$_2$—CH$_2$—C$_6$H$_4$—OH) and phenylpropionyl. In the formula set forth herein, the disulfide bond between the thiol group on the side chain of residue A$_1$ (e.g., Cys or D-Cys) and the thiol group on the side chain of residue A$_9$ (e.g., Cys or D-Cys) is not shown. A peptide of this invention is also denoted herein by another format, e.g., H$_2$-c[Cys-Phe-Phe-D-Trp-Lys-Thr-Phe-Cys]-NH$_2$, with the two disulfide bonded residues (i.e., Cys) placed between the two brackets following "c".

The peptides of the invention can be used to inhibit the release of insulin in a subject (a mammal such as a human patient). Thus, the peptides are useful in the treatment of physiological conditions in which the inhibition of the release of insulin is of benefit, e.g., type II diabetes. Also, peptides of the invention having a Tyr(I) residue can be used to image cells containing somatostatin receptors (e.g., SSTR-5). Such peptides of the invention can be used either in vivo to detect cells having somatostatin receptors (e.g., cancer cells) or in vitro as a radioligand in a somatostatin receptor binding assay.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), polymeric acids (e.g., tannic acid, carboxymethyl cellulose, polylactic, polyglycolic, or copolymers of polylactic-glycolic acids).

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject in need of the peptide. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/00148. Continuous administration can also be obtained using an implantable or external pump (e.g., INFUSAID™ pump) to administer the therapeutic composition. The peptide can be administered prior to bedtime of the patient.

The dose of a peptide of the present invention for treating the above-mentioned diseases or disorders varies depending upon the manner of administration, the age and the body weight of the subject, and the condition of the subject to be treated, and ultimately will be decided by the attending physician or veterinarian. Such an amount of the peptide as determined by the attending physician or veterinarian is referred to herein as a "therapeutically effective amount."

Also contemplated within the scope of this invention is a peptide covered by the above generic formula for both use in treating diseases or disorders associated with the need to inhibit insulin release, e.g., type II diabetes, and use in detecting somatostatin receptors, e.g., radioimaging.

Other features and advantages of the present invention will be apparent from the detailed description and from the claims.

DETAILED DESCRIPTION OF THE INVENTION

The synthesis and use of somatostatin analogs of this invention are well within the ability of a person of ordinary skill in the art. Unless defined otherwise, all technical and scientific terms used herein have the same meaning as commonly understood by one of ordinary skill in the art to which this invention belongs. Also, all publications, patent applications, patents, and other references mentioned herein are incorporated by reference.

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Synthesis of Somatostatin Analogs

The synthesis of short peptides is well examined in the peptide art. See e.g., Stewart, et al., Solid Phase Peptide Synthesis (Pierce Chemical Co., 2d ed., 1984). The following is the synthesis of Analog I. Other peptides of the invention can be prepared in an analogous manner by a person of ordinary skill in the art.

Benzylhydrylamine-polystyrene resin (Advanced ChemTech, Inc., Louisville, Ky.) (1.1 g, 0.5 mmole) in the chloride ion form was placed in the reaction vessel of an Advanced ChemTech ACT 200 peptide synthesizer programmed to deliver the following reagents/solvents: (a) methylene chloride; (b) 33% trifluoroacetic acid in methylene chloride (2 times for 1 and 25 min each); (c) methylene chloride; (d) ethanol; (e) methylene chloride; and (f) 10% triethylamine in chloroform.

The neutralized resin was stirred with Boc-S-4-methylbenzyl-Cys and diisopropylcarbodiimide (1.5 mmole each) in methylene chloride for 1 h and the resulting amino acid resin was then cycled through steps (a) to (f) in the above wash program. The following amino acids (1.5 mmole) were then coupled successively by the same procedure: Boc-Phe, Boc-O-benzyl-Thr, Boc-N-benzyloxycarbonyl-Lys, Boc-D-Trp, Boc-Phe, Boc-Phe, and Boc-S-methylbenzyl-Cys. After washing and drying, the completed resin weighed 1.6 g.

The resin (1.6 g, 0.5 mmole) was then mixed with anisole (5 ml), dithiothreitol (100 mg), and anhydrous hydrogen fluoride (35 ml) at 0° C. and stirred for 45 min. Excess hydrogen fluoride was evaporated rapidly under a stream of dry nitrogen, and the free peptide precipitated and washed with ether. The crude peptide was then dissolved in 500 ml of 90% acetic acid to which was added a concentrated solution of $I_2$/MeOH until a permanent brown color was observed. Excess $I_2$ was removed by addition of ascorbic acid, and the solution evaporated to a small volume which was applied to a column (2.5×90 cm) of SEPHADEX™ G-25 which was eluted with 50% AcOH. Fractions containing a major component by ultraviolet (UV) absorption and thin layer chromatography were then pooled, evaporated to a small volume, and applied to a column (1.5×70 cm) of VYDAC™ octadecylsilane silica (10–15 μm). This column was eluted with a linear gradient from 80 percent A and 20 percent B to 40 percent A and 60 percent B where A is 0.1% trifluoroacetic acid (TFA) in water and B is 79.9% acetonitrile, 20% water, and 0.1% TFA. Fractions were examined by thin layer chromatography (tlc) and analytical high performance liquid chromatography (hplc) and pooled to give maximum purity. Repeated lyophilization of the solution from water gave 95 mg of the product as a white, fluffy powder.

The product is found to be homogenous by hplc and tlc. Amino acid analysis of an acid hydrolysate and matrix-assisted laser desorption mass spectrometry (MALDI MS) confirmed the composition of the cyclic octapeptide (MW calculated, 1077; MW found, 1080).

The following is the synthesis of Analog V. Benzylhydrylamine-polystyrene resin (Advanced ChemTech, Inc.) (0.7 g, 0.25 mmole) in the chloride ion form was placed in the reaction vessel of an Advanced ChemTech ACT 200 peptide synthesizer programmed to deliver the following reagents/solvents: (a) methylene chloride; (b) 33% trifluoroacetic acid in methylene chloride (2 times for 1 and 25 min each); (c) methylene chloride; (d) ethanol; (e) methylene chloride; and (f) 10% triethylamine in chloroform.

The neutralized resin was stirred with Boc-S-methylbenzyl-Cys and diisopropylcarbodiimide (1.5 mmole each) in methylene chloride for 1 h and the resulting amino acid resin was then cycled through steps (a) to (g) in the above wash program. The following amino acids (1.5 mmole) were then coupled successively by the same procedure: Boc-Phe, Boc-O-benzyl-Thr, Boc-N-benzyloxycarbonyl-Lys, Boc-D-Trp, Boc-Phe, Boc-Phe, Boc-Asn, and Boc-S-methylbenzyl-Cys. After washing and drying, the completed resin weighed 1.2 g. The peptide resin was subjected to HF cleavage and $I_2$ cyclization as described above. Column purification, as described above, yielded 21 mg of the cyclic nonapeptide which was found to be homogeneous by hplc and tlc. Amino acid analysis of an acid hydrolysate and MALDI MS confirmed the composition of the cyclic nonapeptide (MW calculated, 1192; found, 1192).

The synthesis of iodinated somatostatin analogs at the tyrosine residue (e.g., the chloramine-T method) is well documented and are within the ability of a person of ordinary skill in the art. See, e.g., Czernick, et al., J. Biol. Chem. 258:5525 (1993) and European Patent No. 389,180 B1.

Somatostatin Receptor Binding Assay (1) Human SSTR-2 Binding Assay:

CHO-K1 (ovary, Chinese hamster) cells were obtained from the American Type Culture Collection (ATCC) (Rockville, Md.) (ATCC No. CCL61) and were transfected with the human SSTR-2 cDNA, described in Yamada, et al., Proc. Natl. Acad. Sci. USA, 89:251–255 (1992) and also available from ATCC (ATCC No. 79046), using standard techniques known in the molecular biological art. See, e.g., Patel, et al., Biochem. Biophys. Res. Commun. 198:605 (1994). Crude membranes were prepared by homogenizing the human SSTR-2 transfected CHO-K1 cells in 20 ml of ice-cold 50 mM Tris-HCl (Buffer A) with a POLYTRON™ homogenizer (Brinkmann Instruments, Westbury, N.Y.) at setting 6, for 15 sec. Additional Buffer A was added to obtain a final volume of 40 ml, and the homogenate was centrifuged in a SORVAL™ SS-34 rotor (DuPont, Newtown, Conn.) at 39,000 g for 10 min at 0–4° C. The resulting supernatant was decanted and discarded. The pellet was rehomogenized in ice-cold Buffer A, diluted, and centrifuged as before. The final pellet was resuspended in the 10 mM Tris HCl and held on ice for the receptor binding assay.

Aliquots of the membrane preparation were incubated for 90 min at 25° C. with 0.05 nM [$^{125}$I-Tyr]MK-678 (2000 Ci/mmol; c[N-methyl-Ala-Tyr($I^{125}$)-D-Trp-Lys-Val-Phe]) in 50 mM HEPES (pH 7.4) containing a test peptide at various concentrations (e.g., $10^{-11}$ to $10^{-6}$ M), 10 mg/ml bovine serum albumin (fraction V, Sigma Chemical Co., St. Louis, Mo.), $MgCl_2$ (5 mM), Trasylol (200 KIU/ml), bacitracin (0.02 mg/ml), and phenylmethyl-sulphonyl fluoride (0.02 mg/ml). The final assay volume was 0.3 ml. The incubations were terminated by rapid filtration through GF/C filters (pre-soaked in 0.3% polyethylenimine for 30 min) using a filtration manifold (Brandel, Gaithersburg, Md.). Each tube and filter was then washed three times with 5 ml aliquots of ice-cold Buffer A. Specific binding was defined as the total [$^{125}$I-Tyr]MK-678 bound minus that bound in the presence of 200 nM somatostatin-14.

The following test peptides were assayed: somatostatin-14, somatostatin-28, Analog I, Analog II, Analog III, Analog IV, and Analog V. The structure of Analogs I–V are shown above. The Ki values for the test peptides were calculated by using the following formula: $K_i=IC_{50}/[1+(LC/LEC)]$ where $IC_{50}$ is the concentration of the test peptide required to inhibit 50 percent of the specific binding of the radioligand [$^{125}$I-Tyr]MK-678, LC is the concentration of the radioligand (0.05 nM), and LEC is the equilibrium dissociation constant of the radioligand (0.155 nM). The $K_i$ values calculated for the test peptides are shown in the column under the heading "SSTR-2" in Table I.

(2) Human SSTR-5 Binding Assay

CHO-K1 cells were transfected with the human SSTR-5 cDNA, described in Yamada, et al., Biochem Biophys. Res.

Commun., 195–844 (1993) using standard techniques known in the molecular biological art. See, e.g., Patel, et al., Biochem. Biophys. Res. Comm. 198:605 (1994). Crude membranes were prepared by homogenization of the human SSTR-5 transfected CHO-K1 cells in 20 ml of ice-cold 50 mM Tris-HCl with a POLYTRON™ homogenizer (setting 6, 15 sec). Buffer was added to obtain a final volume of 40 ml, and the homogenate was centrifuged in a SORVAL™ SS-34 rotor at 39,000 g for 10 min at 0–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test peptide at various concentrations (e.g., $10^{-11}$ to $10^{-6}$ M), 10 mg/ml bovine serum albumin (fraction V), $MgCl_2$ (5 mM), Trasylol (200 KIU/ml), bacitracin (0.02 mg/ml), and phenylmethyl-sulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter was then washed three times with 5 ml aliquots of ice-cold buffer. Specific binding was defined as the total [$^{125}$I-Tyr$^{11}$]somatostatin-14 bound minus that bound in the presence of 1000 nM of the somatostatin type-5 receptor ligand BIM-23052 ($H_2$-D-Phe-Phe-Phe-D-Trp-Lys-Thr-Phe-Thr-$NH_2$). The $K_i$ values for the test peptides were calculated by using the following formula: $IC_{50}/[1+(LC/LEC)]$ where $IC_{50}$ is the concentration of the test peptide required to inhibit 50 percent of the specific binding of the radioligand [$^{125}$I-Tyr$^{11}$]somatostatin-14, LC is the concentration of the radioligand (0.05 nM), and LEC is the equilibrium dissociation constant of the radioligand (0.16 nM). The $K_i$ values calculated for the test peptides are shown in the column under the heading "SSTR-5" in Table I.

Table I also shows the respective ratios of the $K_i$'s for the human SSTR-2 and the $K_i$'s for the human SSTR-5. The peptides of the invention (e.g., Analogs I–V) have ratios unexpectedly greater than one and, thus, are more selective for the SSTR-5 than for the SSTR-2.

TABLE 1

| COMPOUND | SSTR-2 | SSTR-5 | SSTR-2/SSTR-5 |
|---|---|---|---|
| Somatostatin-14 | 0.187 | 0.883 | 0.212 |
| Somatostatin-28 | 0.242 | 0.383 | 0.632 |
| Analog I | 15.1 | 0.376 | 40.2 |
| Analog II | 13.0 | 2.63 | 4.94 |
| Analog III | 14.7 | 1.21 | 12.1 |
| Analog IV | 19.3 | 0.928 | 20.8 |
| Analog V | 129 | 2.43 | 53.1 |

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of inhibiting the release of insulin in a subject in need thereof, which comprises administering to said subject an effective amount of a peptide of the formula:

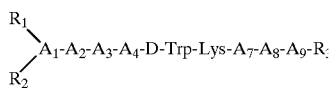

in which $A_1$ is the D- or L-isomer of Cys;

$A_2$ is Asn, Gln, an aliphatic amino acid, an aromatic amino acid or is deleted;

$A_3$ is an aromatic amino acid;

$A_4$ is His or an aromatic amino acid;

$A_7$ is Thr, Ser, or an aliphatic amino acid;

$A_8$ is an aromatic amino acid;

$A^9$ is the D- or L-isomer of Cys;

each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and $R_3$ is $NH_2$, or $NH.Y.CH_2.Z$ where Y is a $C_{1-12}$ hydrocarbon moiety and Z is H, OH, $CO_2H$, or $CONH_2$; and a disulfide bond links the side chains of residues $A_1$ and $A_9$; or a pharmaceutically acceptable salt thereof.

2. A method according to claim 1, wherein said peptide is of the formula:

$H_2$-c[Cys-Phe-Phe-D-Trp-Lys-Thr-Phe-Cys]-$NH_2$, $H_2$-c[D-Cys-Phe-Phe-D-Trp-Lys-Thr-Phe-Cys]-$NH_2$, $H_2$-c[Cys-Phe-Trp-D-Trp-Lys-Ser-Phe-Cys]-$NH_2$, or $H_2$-c[Cys-Phe-Phe-D-Trp-Lys-Ser-Phe-Cys]-$NH_2$.

3. A method according to claim 1, wherein said peptide is of the formula:

$H_2$-c[Cys-Phe-Trp-D-Trp-Lys-Thr-Phe-Cys]-$NH_2$, $H_2$-c[D-Cys-Phe-Trp-D-Trp-Lys-Thr-Phe-Cys]-$NH_2$, $H_2$-c[Cys-Phe-His-D-Trp-Lys-Thr-Phe-Cys]-$NH_2$, $H_2$-c[D-Cys-Phe-His-D-Trp-Lys-Thr-Phe-Cys]-$NH_2$, $H_2$-c[D-Cys-Phe-Phe-D-Trp-Lys-Ser-Phe-Cys]-$NH_2$, $H_2$-c[D-Cys-Phe-Trp-D-Trp-Lys-Ser-Phe-Cys]-$NH_2$, $H_2$-c[Cys-Phe-His-D-Trp-Lys-Ser-Phe-Cys]-$NH_2$, $H_2$-c[D-Cys-Phe-His-D-Trp-Lys-Ser-Phe-Cys]-$NH_2$, $H_2$-c[Cys-Phe-Tyr(I)-D-Trp-Lys-Thr-Phe-Cys]-$NH_2$, $H_2$-c[D-Cys-Phe-Tyr(I)-D-Trp-Lys-Thr-Phe-Cys]-$NH_2$, $H_2$-c[Cys-Phe-Tyr(I)-D-Trp-Lys-Ser-Phe-Cys]-$NH_2$, or $H_2$-c[D-Cys-Phe-Tyr(I)-D-Trp-Lys-Ser-Phe-Cys]-$NH_2$.

4. A method according to claim 1, wherein said peptide is of the formula:

$H_2$-c[Cys-Asn-Phe-Phe-D-Trp-Lys-Thr-Phe-Cys]-$NH_2$, $H_2$-c[D-Cys-Asn-Phe-Phe-D-Trp-Lys-Thr-Phe-Cys]-$NH_2$, $H_2$-c[Cys-Asn-Phe-Trp-D-Trp-Lys-Thr-Phe-Cys]-$NH_2$, $H_2$-c[D-Cys-Asn-Phe-Trp-D-Trp-Lys-Thr-Phe-Cys]-$NH_2$, $H_2$-c[Cys-Asn-Phe-His-D-Trp-Lys-Thr-Phe-Cys]-$NH_2$, $H_2$-c[D-Cys-Asn-Phe-His-D-Trp-Lys-Thr-Phe-Cys]-$NH_2$, $H_2$-c[Cys-Asn-Phe-Phe-D-Trp-Lys-Ser-Phe-Cys]-$NH_2$, $H_2$-c[D-Cys-Asn-Phe-Phe-D-Trp-Lys-Ser-Phe-Cys]-$NH_2$, $H_2$-c[Cys-Asn-Phe-Trp-D-Trp-Lys-Ser-Phe-Cys]-$NH_2$,

H$_2$-c[D-Cys-Asn-Phe-Trp-D-Trp-Lys-Ser-Phe-Cys]-NH$_2$,

H$_2$-c[Cys-Asn-Phe-His-D-Trp-Lys-Ser-Phe-Cys]-NH$_2$,

H$_2$-c[D-Cys-Asn-Phe-His-D-Trp-Lys-Ser-Phe-Cys]-NH$_2$,

H$_2$-c[Cys-Asn-Phe-Tyr(I)-D-Trp-Lys-Thr-Phe-Cys]-NH$_2$,

H$_2$-c[D-Cys-Asn-Phe-Tyr(I)-D-Trp-Lys-Thr-Phe-Cys]-NH$_2$,

H$_2$-c[Cys-Asn-Phe-Tyr(I)-D-Trp-Lys-Ser-Phe-Cys]-NH$_2$, or

H$_2$-c[D-Cys-Asn-Phe-Tyr(I)-D-Trp-Lys-Ser-Phe-Cys]-NH$_2$.

5. A method of treating type II diabetes in a subject in need thereof, which comprises administering to said subject an effective amount of a peptide of the formula:

$$\begin{array}{c} R_1 \\ \diagdown \\ \diagup \\ R_2 \end{array} A_1\text{-}A_2\text{-}A_3\text{-}A_4\text{-D-Trp-Lys-}A_7\text{-}A_8\text{-}A_9\text{-}R_3$$

in which $A_1$ is the D- or L-isomer of Cys;

$A_2$ is Asn, Gln, an aliphatic amino acid, an aromatic amino acid or is deleted;

$A_3$ is an aromatic amino acid;

$A_4$ is His or an aromatic amino acid;

$A_7$ is Thr, Ser, or an aliphatic amino acid;

$A_8$ is an aromatic amino acid;

$A^9$ is the D- or L-isomer of Cys;

each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and $R_3$ is NH$_2$, or NH—Y—CH$_2$—Z where Y is a $C_{1-12}$ hydrocarbon moiety and Z is H, OH, CO$_2$H, or CONH$_2$; and a disulfide bond links the side chains of residues $A_1$ and $A_9$; or a pharmaceutically acceptable salt thereof.

6. A method according to claim 5, wherein said peptide is of the formula:

H$_2$-c[Cys-Phe-Phe-D-Trp-Lys-Thr-Phe-Cys]-NH$_2$,

H$_2$-c[D-Cys-Phe-Phe-D-Trp-Lys-Thr-Phe-Cys]-NH$_2$,

H$_2$-c[Cys-Phe-Trp-D-Trp-Lys-Ser-Phe-Cys]-NH$_2$, or

H$_2$-c[Cys-Phe-Phe-D-Trp-Lys-Ser-Phe-Cys]-NH$_2$.

7. A method according to claim 5, wherein said peptide is of the formula:

H$_2$-c[Cys-Phe-Trp-D-Trp-Lys-Thr-Phe-Cys]-NH$_2$,

H$_2$-c[D-Cys-Phe-Trp-D-Trp-Lys-Thr-Phe-Cys]-NH$_2$,

H$_2$-c[Cys-Phe-His-D-Trp-Lys-Thr-Phe-Cys]-NH$_2$,

H$_2$-c[D-Cys-Phe-His-D-Trp-Lys-Thr-Phe-Cys]-NH$_2$,

H$_2$-c[D-Cys-Phe-Phe-D-Trp-Lys-Ser-Phe-Cys]-NH$_2$,

H$_2$-c[D-Cys-Phe-Trp-D-Trp-Lys-Ser-Phe-Cys]-NH$_2$,

H$_2$-c[Cys-Phe-His-D-Trp-Lys-Ser-Phe-Cys]-NH$_2$,

H$_2$-c[D-Cys-Phe-His-D-Trp-Lys-Ser-Phe-Cys]-NH$_2$,

H$_2$-c[Cys-Phe-Tyr(I)-D-Trp-Lys-Thr-Phe-Cys]-NH$_2$,

H$_2$-c[D-Cys-Phe-Tyr(I)-D-Trp-Lys-Thr-Phe-Cys]-NH$_2$,

H$_2$-c[Cys-Phe-Tyr(I)-D-Trp-Lys-Ser-Phe-Cys]-NH$_2$, or

H$_2$-c[D-Cys-Phe-Tyr(I)-D-Trp-Lys-Ser-Phe-Cys]-NH$_2$.

8. A method according to claim 5, wherein said peptide is of the formula:

H$_2$-c[Cys-Asn-Phe-Phe-D-Trp-Lys-Thr-Phe-Cys]-NH$_2$,

H$_2$-c[D-Cys-Asn-Phe-Phe-D-Trp-Lys-Thr-Phe-Cys]-NH$_2$,

H$_2$-c[Cys-Asn-Phe-Trp-D-Trp-Lys-Thr-Phe-Cys]-NH$_2$,

H$_2$-c[D-Cys-Asn-Phe-Trp-D-Trp-Lys-Thr-Phe-Cys]-NH$_2$,

H$_2$-c[Cys-Asn-Phe-His-D-Trp-Lys-Thr-Phe-Cys]-NH$_2$,

H$_2$-c[D-Cys-Asn-Phe-His-D-Trp-Lys-Thr-Phe-Cys]-NH$_2$,

H$_2$-c[Cys-Asn-Phe-Phe-D-Trp-Lys-Ser-Phe-Cys]-NH$_2$,

H$_2$-c[D-Cys-Asn-Phe-Phe-D-Trp-Lys-Ser-Phe-Cys]-NH$_2$,

H$_2$-c[Cys-Asn-Phe-Trp-D-Trp-Lys-Ser-Phe-Cys]-NH$_2$,

H$_2$-c[D-Cys-Asn-Phe-Trp-D-Trp-Lys-Ser-Phe-Cys]-NH$_2$,

H$_2$-c[Cys-Asn-Phe-His-D-Trp-Lys-Ser-Phe-Cys]-NH$_2$,

H$_2$-c[D-Cys-Asn-Phe-His-D-Trp-Lys-Ser-Phe-Cys]-NH$_2$,

H$_2$-c[Cys-Asn-Phe-Tyr(I)-D-Trp-Lys-Thr-Phe-Cys]-NH$_2$,

H$_2$-c[D-Cys-Asn-Phe-Tyr(I)-D-Trp-Lys-Thr-Phe-Cys]-NH$_2$,

H$_2$-c[Cys-Asn-Phe-Tyr(I)-D-Trp-Lys-Ser-Phe-Cys]-NH$_2$, or

H$_2$-c[D-Cys-Asn-Phe-Tyr(I)-D-Trp-Lys-Ser-Phe-Cys]-NH$_2$.

9. A pharmaceutical composition comprising a pharmaceutically acceptable carrier and an effective amount of a peptide of the formula:

$$\begin{array}{c} R_1 \\ \diagdown \\ \diagup \\ R_2 \end{array} A_1\text{-}A_2\text{-}A_3\text{-}A_4\text{-D-Trp-Lys-}A_7\text{-}A_8\text{-}A_9\text{-}R_3$$

in which $A_1$ is the D- or L-isomer of Cys;

$A_2$ is Asn, Gln, an aliphatic amino acid, an aromatic amino acid or is deleted;

$A_3$ is an aromatic amino acid;

$A_4$ is His or an aromatic amino acid;

$A_7$ is Thr, Ser, or an aliphatic amino acid;

$A_8$ is an aromatic amino acid;

$A^9$ is the D- or L-isomer of Cys;

each of $R_1$ and $R_2$ is, independently, H, $C_{1-12}$ alkyl, $C_{7-20}$ phenylalkyl, $C_{11-20}$ naphthylalkyl, C-12 hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and $R_3$ is NH$_2$, or NH—Y—CH$_2$—Z where Y is a $C_{1-12}$ hydrocarbon moiety and Z is H, OH, CO$_2$H, or CONH$_2$; and a disulfide bond links the side chains of residues $A_1$ and $A_9$; or a pharmaceutically acceptable salt thereof.

10. A pharmaceutical composition according to claim 9, wherein said peptide is of the formula:

H₂-c[Cys-Phe-Phe-D-Trp-Lys-Thr-Phe-Cys]-NH₂,
H₂-c[D-Cys-Phe-Phe-D-Trp-Lys-Thr-Phe-Cys]-NH₂,
H₂-c[Cys-Phe-Trp-D-Trp-Lys-Ser-Phe-Cys]-NH₂, or
H₂-c[Cys-Phe-Phe-D-Trp-Lys-Ser-Phe-Cys]-NH₂.

11. A pharmaceutical composition according to claim 9, wherein said peptide is of the formula:
H₂-c[Cys-Phe-Trp-D-Trp-Lys-Thr-Phe-Cys]-NH₂,
H₂-c[D-Cys-Phe-Trp-D-Trp-Lys-Thr-Phe-Cys]-NH₂,
H₂-c[Cys-Phe-His-D-Trp-Lys-Thr-Phe-Cys] -NH₂,
H₂-c[D-Cys-Phe-His-D-Trp-Lys-Thr-Phe-Cys]-NH₂,
H₂-c[D-Cys-Phe-Phe-D-Trp-Lys-Ser-Phe-Cys]-NH₂,
H₂-c[D-Cys-Phe-Trp-D-Trp-Lys-Ser-Phe-Cys]-NH₂,
H₂-c[Cys-Phe-His-D-Trp-Lys-Ser-Phe-Cys]-NH₂,
H₂-c[D-Cys-Phe-His-D-Trp-Lys-Ser-Phe-Cys]-NH₂,
H₂-c[Cys-Phe-Tyr(I)-D-Trp-Lys-Thr-Phe-Cys]-NH₂,
H₂-c[D-Cys-Phe-Tyr(I)-D-Trp-Lys-Thr-Phe-Cys]-NH₂,
H₂-c[Cys-Phe-Tyr(I)-D-Trp-Lys-Ser-Phe-Cys]-NH₂, or
H₂-c[D-Cys-Phe-Tyr(I)-D-Trp-Lys-Ser-Phe-Cys]-NH₂.

12. A pharmaceutical composition according to claim 9, wherein said peptide is of the formula:
H₂-c[Cys-Asn-Phe-Phe-D-Trp-Lys-Thr-Phe-Cys]-NH₂,
H₂-c[D-Cys-Asn-Phe-Phe-D-Trp-Lys-Thr-Phe-Cys]-NH₂,
H₂-c[Cys-Asn-Phe-Trp-D-Trp-Lys-Thr-Phe-Cys]-NH₂,
H₂-c[D-Cys-Asn-Phe-Trp-D-Trp-Lys-Thr-Phe-Cys]-NH₂,
H₂-c[Cys-Asn-Phe-His-D-Trp-Lys-Thr-Phe-Cys]-NH₂,
H₂-c[D-Cys-Asn-Phe-His-D-Trp-Lys-Thr-Phe-Cys]-NH₂,
H₂-c[Cys-Asn-Phe-Phe-D-Trp-Lys-Ser-Phe-Cys]-NH₂,
H₂-c[D-Cys-Asn-Phe-Phe-D-Trp-Lys-Ser-Phe-Cys]-NH₂,
H₂-c[Cys-Asn-Phe-Trp-D-Trp-Lys-Ser-Phe-Cys]-NH₂,
H₂-c[D-Cys-Asn-Phe-Trp-D-Trp-Lys-Ser-Phe-Cys]-NH₂,
H₂-c[Cys-Asn-Phe-His-D-Trp-Lys-Ser-Phe-Cys]-NH₂,
H₂-c[D-Cys-Asn-Phe-His-D-Trp-Lys-Ser-Phe-Cys]-NH₂,
H₂-c[Cys-Asn-Phe-Tyr(I)-D-Trp-Lys-Thr-Phe-Cys]-NH₂,
H₂-c[D-Cys-Asn-Phe-Tyr(I)-D-Trp-Lys-Thr-Phe-Cys]-NH₂,
H₂-c[Cys-Asn-Phe-Tyr(I)-D-Trp-Lys-Ser-Phe-Cys]-NH₂, or
H₂-c[D-Cys-Asn-Phe-Tyr(I)-D-Trp-Lys-Ser-Phe-Cys]-NH₂.

13. A method of imaging cells in vivo containing somatostatin receptors comprising administering a peptide of the formula:

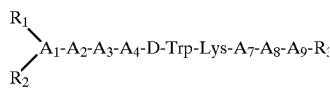

in which
$A_1$ is the D- or L-isomer of Cys;
$A_2$ is Asn, Gln, an aliphatic amino acid, an aromatic amino acid or is deleted;
$A_3$ is an aromatic amino acid;
$A_4$ is His or an aromatic amino acid;
$A_7$ is Thr, Ser, or an aliphatic amino acid;
$A_8$ is an aromatic amino acid;
$A^9$ is the D- or L-isomer of Cys;
each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and
$R_3$ is $NH_2$, or $NH—Y—CH_2—Z$ where Y is a $C_{1-12}$ hydrocarbon moiety and Z is H, OH, $CO_2H$, or $CONH_2$; and
a disulfide bond links the side chains of residues $A_1$ and $A_9$; or a pharmaceutically acceptable salt thereof, provided that at least one aromatic amino acid of the formula Tyr(I) is present in the peptide;
to a subject and detecting the presence of said peptide in said subject.

14. A method according to claim 13, wherein said peptide is of the formula:
H₂-c[Cys-Phe-Tyr(I)-D-Trp-Lys-Thr-Phe-Cys]-NH₂,
H₂-c[D-Cys-Phe-Tyr(I)-D-Trp-Lys-Thr-Phe-Cys]-NH₂,
H₂-c[Cys-Phe-Tyr(I)-D-Trp-Lys-Ser-Phe-Cys]-NH₂,
H₂-c[D-Cys-Phe-Tyr(I)-D-Trp-Lys-Ser-Phe-Cys]-NH₂,
H₂-c[Cys-Asn-Phe-Tyr (I)-D-Trp-Lys-Thr-Phe-Cys]-NH₂,
H₂-c[D-Cys-Asn-Phe-Tyr(I)-D-Trp-Lys-Thr-Phe-Cys]-NH₂,
H₂-c[Cys-Asn-Phe-Tyr(I)-D-Trp-Lys-Ser-Phe-Cys]-NH₂, or
H₂-c[D-Cys-Asn-Phe-Tyr(I)-D-Trp-Lys-Ser-Phe-Cys]-NH₂.

15. A method of imaging cells in vitro containing somatostatin receptors comprising administering a peptide of the formula:

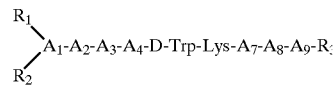

in which
$A_1$ is the D- or L-isomer of Cys;
$A_2$ is Asn, Gln, an aliphatic amino acid, an aromatic amino acid or is deleted;
$A_3$ is an aromatic amino acid;
$A_4$ is His or an aromatic amino acid;
$A_7$ is Thr, Ser, or an aliphatic amino acid;
$A_8$ is an aromatic amino acid;
$A^9$ is the D- or L-isomer of Cys;
each of $R_1$ and $R_2$ is, independently, H, $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, $C_{11-20}$ hydroxynaphthylalkyl, or $COE_1$ where $E_1$ is $C_{1-12}$ alkyl, $C_{7-20}$ phenylalkyl, $C_{11-20}$ naphthylalkyl, $C_{1-12}$ hydroxyalkyl, $C_{7-20}$ hydroxyphenylalkyl, or $C_{11-20}$ hydroxynaphthylalkyl; and
$R_3$ is $NH_2$, or $NH—Y.CH_2—Z$ where Y is a $C_{1-12}$ hydrocarbon moiety and Z is H, OH, $CO_2H$, or $CONH_2$; and
a disulfide bond links the side chains of residues $A_1$ and $A_9$; or a pharmaceutically acceptable salt thereof, provided that at least one aromatic amino acid of the formula Tyr(I), wherein said iodine is radioactive iodine, $^{125}$I, $^{127}$I or $^{131}$I, is present in the peptide; to cells and detecting the presence of said peptide in said cells.

16. A method according to claim 15, wherein said peptide is of the formula:

H$_2$-c[Cys-Phe-Tyr(I)-D-Trp-Lys-Thr-Phe-Cys]-NH$_2$,
H$_2$-c[D-Cys-Phe-Tyr(I)-D-Trp-Lys-Thr-Phe-Cys]-NH$_2$,
H$_2$-c[Cys-Phe-Tyr(I)-D-Trp-Lys-Ser-Phe-Cys]-NH$_2$,
H$_2$-c[D-Cys-Phe-Tyr(I)-D-Trp-Lys-Ser-Phe-Cys]-NH$_2$,
H$_2$-c[Cys-Asn-Phe-Tyr(I)-D-Trp-Lys-Thr-Phe-Cys]-NH$_2$,
H$_2$-c[D-Cys-Asn-Phe-Tyr(I)-D-Trp-Lys-Thr-Phe-Cys]-NH$_2$,
H$_2$-c[Cys-Asn-Phe-Tyr(I)-D-Trp-Lys-Ser-Phe-Cys]-NH$_2$, or
H$_2$-c[D-Cys-Asn-Phe-Tyr(I)-D-Trp-Lys-Ser-Phe-Cys]-NH$_2$.

* * * * *